United States Patent [19]

Wolzinger et al.

[11] Patent Number: 5,605,546
[45] Date of Patent: Feb. 25, 1997

[54] APPARATUS AND METHODS FOR PROTECTING INDWELLING MEDICAL DEVICES

[76] Inventors: Renah Wolzinger, 4212 Silliman Dr.; Ezekiel Joseph, 16242 Typhoon La., both of Huntington Beach, Calif. 92649

[21] Appl. No.: 345,495

[22] Filed: Nov. 28, 1994

[51] Int. Cl.$^6$ .................................................. A61M 5/00
[52] U.S. Cl. .......................................... 604/174; 604/180
[58] Field of Search ................................... 604/174, 180, 604/332, 334, 336; 128/849, 850, 851, 852, 853

[56] References Cited

U.S. PATENT DOCUMENTS

| | | | |
|---|---|---|---|
| 2,928,393 | 3/1960 | Marsan | 604/334 |
| 3,423,277 | 1/1969 | Dipner | 128/849 X |
| 3,455,302 | 7/1969 | Liloila et al. | 128/849 |
| 3,973,565 | 8/1976 | Steer | 604/180 |
| 4,392,853 | 7/1983 | Muto. | |
| 4,569,329 | 2/1986 | Annis | 604/180 |
| 4,605,397 | 8/1986 | Ligon et al. | 604/174 X |
| 4,666,432 | 5/1987 | McNeish et al. | 604/174 |
| 4,742,824 | 5/1988 | Payton et al. | 604/174 X |
| 4,795,435 | 1/1989 | Steer | 604/332 X |
| 4,941,882 | 7/1990 | Ward et al. | 604/180 |
| 4,966,168 | 10/1990 | Glassman | 128/849 X |
| 5,232,453 | 8/1993 | Plass et al. . | |
| 5,354,282 | 11/1994 | Bierman | 604/180 |

FOREIGN PATENT DOCUMENTS

| | | | |
|---|---|---|---|
| WO9117733 | 11/1991 | WIPO. | |
| WO93/17642 | 9/1993 | WIPO | 604/332 |

OTHER PUBLICATIONS

AARP Pharmacy Service, 1994 Catalog, pp. 57–64.

*Primary Examiner*—Sam Rimell
*Attorney, Agent, or Firm*—Frank J. Uxa

[57] ABSTRACT

Apparatus for protecting the outwardly extending portion, for example, the distal end, of an indwelling medical treatment device, for example, a catheter, are disclosed. Such apparatus include an at least partially transparent receptacle defining a chamber sized and adapted to receive an outwardly extending portion of an indwelling medical treatment device, an inlet in the receptacle through which the outwardly extending portion is passed to be received by the chamber, and a securement member on the receptacle adapted to be secured to the human or animal patient so as to substantially prevent liquid contamination of the outwardly extending portion received in the chamber.

22 Claims, 2 Drawing Sheets

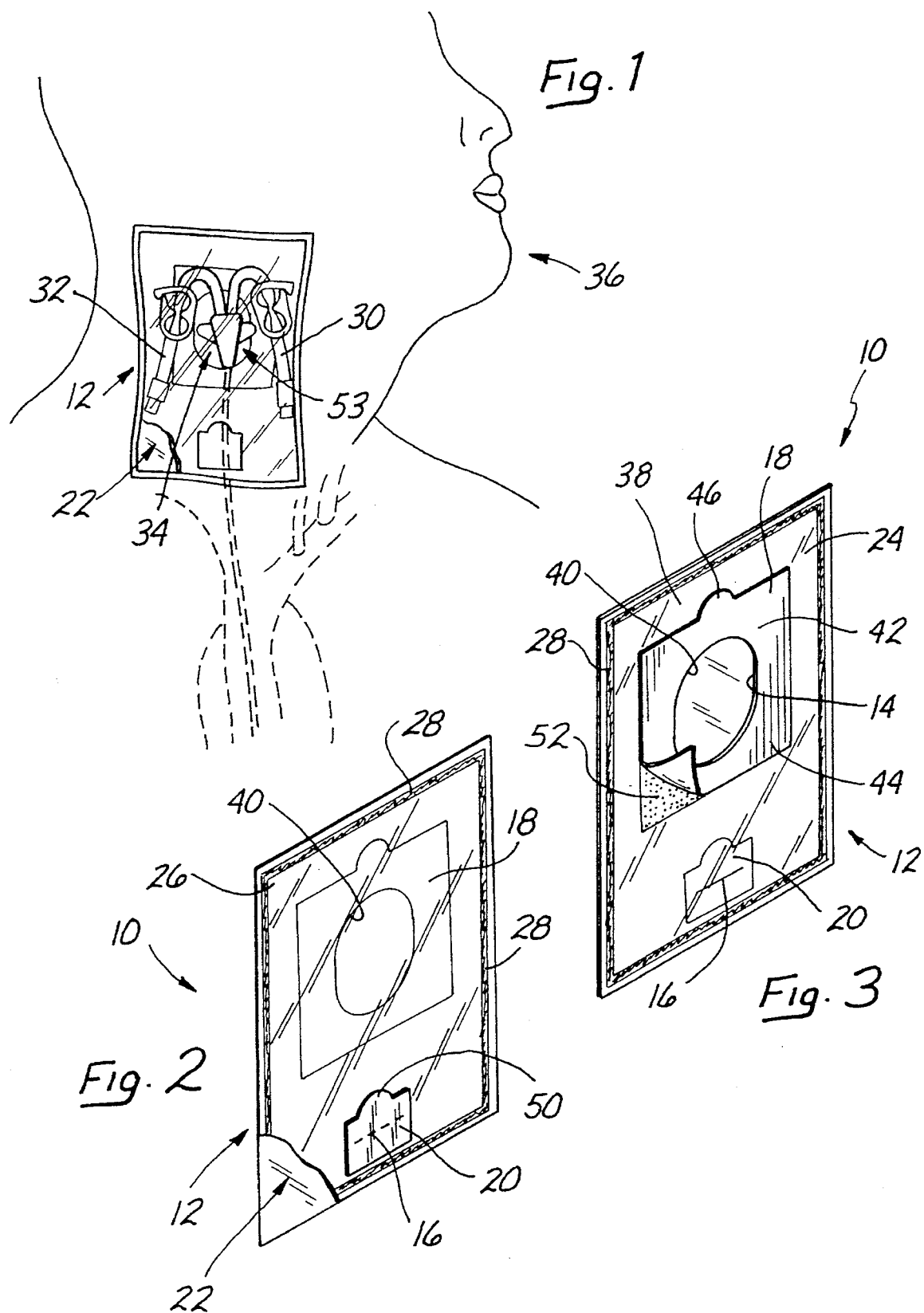

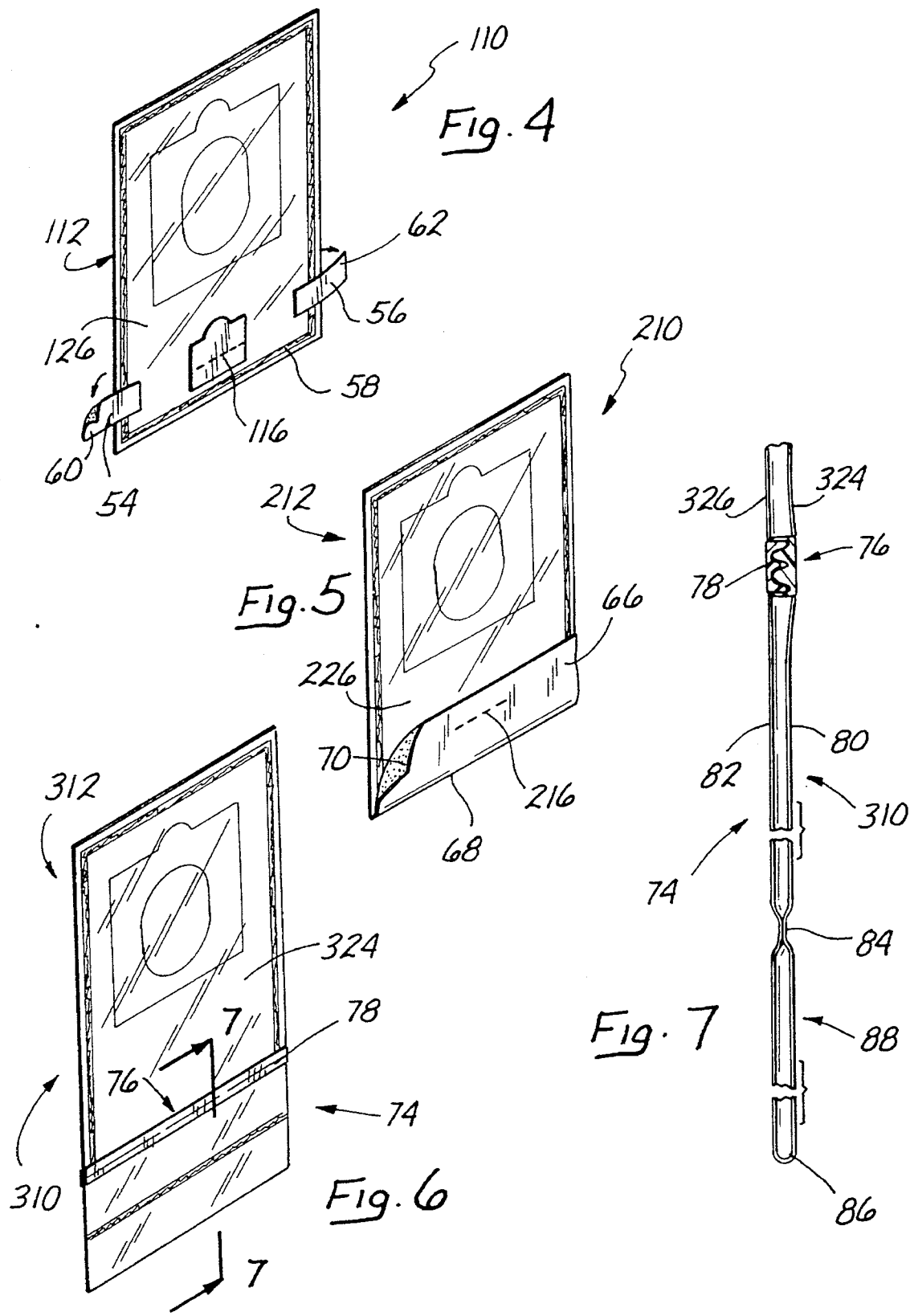

APPARATUS AND METHODS FOR PROTECTING INDWELLING MEDICAL DEVICES

BACKGROUND OF THE INVENTION

This invention is directed to apparatus and methods useful for caring for medical devices, such as catheters, which are indwelling, that is which are partially located within the body of a human or animal. More particularly, the invention is directed to apparatus and methods useful for caring for, for example, covering and/or protecting, the outwardly extending portions of such indwelling medical devices, for example, protecting such outwardly extending portions from one or more potentially harmful environmental factors.

Modern medical science increasingly uses treatment devices, such as catheters, which are partially located in the body of the human or animal undergoing treatment for an extended period of time, on the order of weeks or even months. Oncology patients undergoing chronic chemotherapy and kidney dialysis patients are but two examples of medical patients who often use indwelling catheters, for example, catheters which have one, two or more lumens. Between medical treatments, the outwardly extending portions (or distal ends) of such indwelling medical treatment devices (catheters), which are integral parts of the devices but extend outside the body of the human or animal, are capped, for example, clamped or otherwise closed, to provide some degree of protection for the medical device. As the human or animal goes about the day-to-day activities of life, the capped outwardly extending portions are subjected to moisture and other environmental factors which can contaminate the medical devices and/or can at least potentially cause harm to the devices and/or patients.

Currently, health care personnel protect the distal ends of indwelling catheters by placing commercially available bandages and similar coverings over the exit site (that is at the site of the body of the human or animal patient from which the portion of the medical treatment device (catheter) extends outwardly) and/or placing medical tape over the catheter while leaving the capped catheter ends exposed. Such practices provide little or no real protection, for example, no effective moisture barrier, to the catheter ends, are useful only as a short-term expedient, and can be difficult and painful, and possibly irritating, to remove, for example, from sensitive skin. It would be advantageous to provide more effective systems to care for such outwardly extending portions of indwelling medical treatment devices.

SUMMARY OF THE INVENTION

New apparatus and methods useful for caring for the outwardly extending portions of medical treatment devices partially located within the body of a human or animal have been discovered. The present apparatus are straightforward in construction, are inexpensive to produce and provide an effective cover over the outwardly extending portions of indwelling medical treatment devices and the exit sites which can be maintained in place for relatively long periods of time. The present apparatus are durable and convenient in use so that they can be used for relatively long periods of time or replaced frequently and used only, for example, when the patient is showering or bathing. When in use, the present apparatus have one or more beneficial effects on the human or animal patients. For example, the apparatus can make the patient more comfortable, or at least more able to accept the presence of such indwelling medical treatment devices. Also, the presence of such apparatus advantageously reduces the tendency of the patients to frequently touch the outwardly extending portions with their hands, which touching can damage or otherwise harm the medical treatment devices.

The present apparatus is preferably adapted to facilitate visual inspection of, and/or to allow access to, the outwardly extending portions of the indwelling medical treatment devices while the apparatus remain in place. The present methods are easy to practice and provide effective covering and/or protection without causing harm to the medical treatment devices or patients. In short, the present invention provides substantial advantages and benefits not suggested in the prior art.

In one broad aspect of the invention, apparatus useful for caring for the outwardly extending portion of a device partially located within the body of a human or animal comprise a receptacle, an inlet, and a securement member. The receptacle defines a chamber sized and adapted to receive the outwardly extending portion of a medical treatment device, for example, the distal end or ends of a catheter, partially located within the body of a human or animal. At least a portion of the receptacle is preferably transparent. More preferably, at least a major portion, that is at least about 50%, and still more preferably substantially all, of the receptacle is transparent. The use of an at least partially transparent receptacle is very advantageous in that the portion of the indwelling medical treatment device located in the chamber can be visually inspected and/or monitored through the receptacle without removing or even opening the receptacle.

Having the receptacle at least partially transparent distinguishes the present apparatus from ostomy bags currently in use. In general, such ostomy bags are opaque since there is no need to visually monitor the waste products being collected. In addition, ostomy bags often have a vent to allow fluid, in particular, gas, to escape from the bag as waste products are collected. In a particularly useful embodiment, the present apparatus includes no vent which allows continuous passage of fluid, for example, gas, out of the chamber when the securement member is secured to the body of the human or animal in question. Also, it is preferred that the receptacle be made of a single ply or layer of material which is not covered, or otherwise reinforced, when in use. In contrast, ostomy bags often include two or more plies of material to provide a suitably reinforced structure for the collection of waste products.

The receptacle is made of a material or combination of materials which is effective to act as a cover for the outwardly extending portion of the medical treatment device, and preferably to act as a liquid seal, for example, a liquid water seal, when the present apparatus is in use. Particularly useful materials of construction include polymeric materials, such as thermoplastic polymeric materials. A very useful material of construction is low density polyethylene.

The receptacle preferably includes two sheets of polymeric material film joined or bonded, for example, heat sealed, adhesively sealed, ultrasonically sealed and the like, together at or near at least portions of the peripheral edges to form the receptacle which defines the chamber.

The inlet of the present apparatus is located in the receptacle and is positioned so that the outwardly extending portion of the indwelling device can be passed through the inlet to be received in the chamber.

The inlet in the receptacle may have any suitable size and/or configuration. The inlet should have sufficient size to allow the outwardly extending portion of the indwelling device to be passed therethrough into the chamber defined by the receptacle. However, the inlet should not be overly big since this is unnecessary and may result in requiring an excessively large securement member to secure the receptacle to the human or animal. Although not required, it is preferred that the inlet have a substantially circular configuration. This provides for ease of manufacture and is very convenient in use.

The securement member of the present apparatus is located on the receptacle and is adapted to be secured to the body of the human or animal in whose body the device is partially located. In one embodiment, the receptacle is adapted to cover the outwardly extending portion received in the chamber when the securement member is secured to the body of the human or animal. In a particularly useful embodiment, the receptacle is adapted to protect the outwardly extending portion received in the chamber from one or more environmental factors, e.g., liquid water or moisture, outside the receptacle when the securement member is secured to the body of the human or animal.

The securement member preferably substantially surrounds the inlet. In a very useful embodiment, the securement member, for example, an adhesive securement member, surrounds the inlet in close proximity to the inlet. Particularly useful securement members are those which are adapted to be adhesively secured to the body of a human or animal.

The present apparatus may include at least one additional securement member located on the receptacle and spaced apart from the securement member. This additional securement member is adapted to be secured to the body of the human or animal, for example, to more firmly secure the receptacle to the human or animal. Such additional securement member or members are particularly useful when it is desired to have the receptacle (and the contained outwardly extending portion of the indwelling medical treatment device) positioned substantially flat against the body of the human or animal rather than being positioned to extend away from the body of the human or animal. This feature can increase the comfort level of the patient in whose body the indwelling medical treatment device is located.

The securement member and additional securement member or members are preferably secured to the receptacle. This securing or bonding of the securement member and additional securement member or members to the receptacle can be accomplished in a suitable manner. For example, the securement member and additional securement member or members are can be bonded to the receptacle by one or more of the following: an adhesive component, thermal bonding techniques, ultrasonic bonding techniques and the like. A very useful securement member is one made of a double-sided medical adhesive tape with one adhesive side located on and adhesively secured to the receptacle. The other adhesive side of the tape is available to be adhesively secured to the human or animal. This tape preferably has a pull tab to provide for easy removal of the transfer adhesive from the tape. Thus, when it is desired to secure the receptacle to the human or animal, the pull tab is employed to remove the transfer adhesive and the tape secured to the receptacle is applied to the human or animal to provide the desired securement.

In one embodiment of the apparatus, a closeable outlet in the receptacle is provided. This closeable outlet is adapted, when open, to allow access to the outwardly extending portion of the indwelling device passing through the inlet while the securement member is secured to the body of a human or animal. This closeable outlet is preferably adapted so that, when closed, the closeable outlet assists in covering and/or protecting the outwardly extending portion received in the chamber. This embodiment is particularly useful when it is desired to cover and/or protect the outwardly extending portion and the exit site on the human or animal for a relatively long period of time, for example, on the order of up to about 5 or about 10 days. Thus, the patient, human or animal, on whom the apparatus is secured, can undergo several medical treatments during this period of time while the apparatus remains secured in place. The outwardly extending portion of the indwelling device can be accessed through the closeable outlet, to facilitate such treatments. Once the closeable outlet is re-closed, the receptacle regains and maintains its covering and/or protective characteristics so that it is effective for continued use. In addition, the use of such a closeable outlet is well suited to patients who have sensitive skin around the exit site to reduce or even eliminate skin irritation caused by frequent removals of the entire apparatus.

In one useful embodiment, the receptacle includes a first sidewall and a substantially opposing second sidewall. The inlet is located in the first sidewall, and is preferably centered toward one end of the first sidewall. When a closable outlet is included, it is preferably located in the second sidewall, and is preferably centered toward the opposing end (opposite of the above-noted one end of the first sidewall). Thus, when the present apparatus is in use and secured to the body of the human or animal patient, the closable outlet is facing away from the patient's body so as to facilitate accessing the outwardly extending portion in the chamber through the closable outlet.

In the embodiments of the present apparatus including a closeable outlet, it is preferred that the apparatus further comprise a closure assembly, for example, an adhesive element, sized and adapted to be positioned to maintain the closeable outlet closed and to be manipulated, for example, moved or removed, to allow the closeable outlet to be opened. To illustrate, a piece of single-sided adhesive tape may have a pull tab which can be manipulated or activated, for example, manually pulled, to remove the tape from the closable outlet, to open the closeable outlet and, after the desired access to the outwardly extending portion has been had, can be used to replace the tape relative to, for example, over, the closeable outlet to effectively close or reseal the closeable outlet. Other closure assembly structures may be employed.

The transparent receptacle can be employed alone or in combination with the closeable outlet as described herein. In addition, unless expressly stated otherwise or unless two or more features are mutually inconsistent, each of the features described herein can be used in combination with any one or more of the other features described herein, and all such apparatus and methods are within the scope of the present invention.

Methods for caring for the outwardly extending portion of a medical treatment device partially located within the body of a human or animal are provided and are included within the scope of the present invention. Such methods comprise providing an apparatus comprising a receptacle defining a chamber, an inlet in the receptacle leading to the chamber and a securement member located on the receptacle. Particularly useful apparatus are the apparatus of the present invention described herein. In any event, the present methods further comprise passing the outwardly extending portion of the medical treatment device through the inlet into the chamber, and securing the securement member to the body of the human or animal. In one embodiment, this securing step is effective to cover the outwardly extending portion received in the chamber and/or to protect the outwardly extending portion received in the chamber from one or more environmental factors outside the receptacle. The outwardly extending portion of the medical treatment device is preferably the distal end or ends of an indwelling medical treatment catheter, for example, such a catheter including one lumen or more than one, such as two or three, lumens.

In a particularly useful embodiment of the present methods, the protection apparatus includes a closeable outlet in the receptacle and the methods further comprise opening the closeable outlet while the securement member is secured to the body of the human or animal to access the outwardly extending portion passing through the inlet and, thereafter, closing the closeable outlet.

The present methods very effectively care for, for example, cover and/or protect, the outwardly extending portions of indwelling medical treatment devices while, at the same time, conveniently allowing access to such outwardly extending portion when such access is needed, for example, to provide a desired or needed medical treatment.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is an illustration showing an embodiment of the present apparatus in use, with a portion of a sidewall broken away.

FIG. 2 is a side view, in perspective, of the embodiment of the present apparatus shown in FIG. 1 prior to use, with a portion of a sidewall broken away.

FIG. 3 is an opposing side view, in perspective, of the embodiment of the present apparatus shown in FIG. 1 prior to use.

FIG. 4 is a side view, in perspective, of another embodiment of the present apparatus shown prior to use.

FIG. 5 is a side view, in perspective, of an alternate embodiment of the present apparatus shown prior to use.

FIG. 6 is a side view, in perspective, of a further embodiment of the present apparatus shown prior to use.

FIG. 7 is a view taken generally along line 7—7 of FIG. 6.

DETAILED DESCRIPTION OF THE DRAWINGS

Referring now to the drawings, and in particular to FIGS. 2 and 3, the present apparatus, shown generally at 10, includes a receptacle 12, an inlet 14, an outlet 16, a securement element 18 and a removable outlet cover 20. Receptacle 12 defines a chamber 22.

Receptacle 12 includes a first transparent sidewall 24 and an opposing second transparent sidewall 26. Sidewalls 24 and 26 are made of low density polyethylene film and are sealed together at their peripheries by a conventional heat sealing technique which forms peripheral seal 28. As so configured, receptacle 12 defines chamber 22 located between first and second sidewalls 24 and 26, respectively, and which is bordered by peripheral seal 28. Each of the sidewalls 24 and 26 is made of a single ply of material and is not otherwise reinforced.

First sidewall 24 includes circular inlet 14 which provides access into chamber 22. Inlet 14 can have any suitable configuration and size provided that it functions as described herein. As shown in FIG. 3, inlet 14 is centered toward one end of first sidewall 24. Inlet 14 is sufficiently large to allow the distal ends 30 and 32 of indwelling catheter 34, which, as shown in FIG. 1, is located in the jugular vein of patient 36, to pass into chamber 22. Care should be taken to avoid having inlet 14 excessively big because, for example, the larger this outlet is the more difficult it is to seal, when desired.

Securement element 18 is a substantially rectangular piece of double-sided medical tape, which is adhesively secured to the external surface 38 of first sidewall 24. Securement member 19 can have any suitable configuration and size provided that it functions as described herein. Securement element 18 includes a through hole 40 which is substantially coincidental with inlet 14. In other words, the securement element 18, with hole 40, substantially surrounds inlet 14 in close proximity to the periphery of the inlet. Care should be taken in sizing securement member 18. Thus, securement member 18 should be sufficiently large, for example, have a sufficiently large adhesive area, to provide for a firm and sealing securement of receptacle 12 to the patient, when desired. However, securement member should not be excessively large since this may result in difficulty in removing the receptacle 12 from the patient, when such removal is desired, and/or may increase the risk of irritating the skin of the patient.

Securement element 18 includes a cover 42 which includes a non-adhesive outer surface 44. In addition, securement element 18, and in particular cover 42, includes a pull tab 46 which may be labeled as such, that is with the word PULL.

Outlet 16 is located or centered toward the opposing end, as shown in FIG. 3, of second sidewall 26 and provides limited access to chamber 22. Removable outlet cover 20 comprises a piece of single-sided medical adhesive tape which, when in place as shown in FIGS. 2 and 3, completely covers or seals outlet 16. Removable outlet cover 20 includes a pull tab 50 which may be labeled as such, that is with the word PULL.

During manufacture, apparatus 10 is sterilized, for example, using a conventional sterilization technique for medical goods containing polymeric materials and adhesive tape, to render the apparatus sterile, and is packaged so as to maintain the apparatus sterile prior to use.

Apparatus 10 is used and functions as follows. When it is desired to protect the distal ends 30 and 32 of indwelling catheter 34 from the environment, for example, in between medical treatments and/or during bathing or strenuous activity, protection apparatus 10 is employed. Distal ends 30 and 32 are capped and/or clamped shut (as is conventionally done) to protect the interior of catheter 34 at least to some extent from contamination.

Apparatus 10 is removed from its packaging. The pull tab 46 on securement element 18 is manually pulled to remove cover 42 and expose adhesive surface 52. With this accomplished, the distal ends 30 and 32, which extend outside patient 36 at exit site 53, are passed through inlet 14 into chamber 22, as shown in FIG. 1. After this has been accomplished, adhesive surface 52 is brought into contact with the skin of patient 36 to adhere the receptacle 12 to the patient. At this point, the distal ends 30 and 32 are within chamber 22, inlet 14 surrounds exit site 53 and is sealed, and the receptacle 12 acts as a cover for the distal ends and protects the distal ends from environmental moisture (liquid water) from outside receptacle 12.

With receptacle 12 in place, as shown in FIG. 1, the distal ends 30 and 32 of catheter 34 and exit cite 53 have a substantially increased degree of protection against contamination by environmental moisture and other environmental factors. In addition, because sidewalls 24 and 26 are transparent, the status of distal ends 30 and 32 and exit site 53 can be visually monitored without having to remove receptacle 12 from patient 36. With receptacle 12 secured to patient 36, the patient can go about his/her day-to-day activities (or some specific activity, such as bathing) with an increased degree of comfort and being confident that the catheter 34 and exit site 53 will not be adversely affected.

When it is desired to access the distal ends 30 and 32 of indwelling catheter 34, for example, to perform a necessary medical treatment on patient 36, the receptacle 12 can be removed from patient 36 and the distal ends removed from chamber 22. In this instance, after such removal, receptacle 12 is discarded. After the medical treatment has occurred, a new apparatus 10 can be employed, as described above, to again protect distal ends 30 and 32 from environmental factors. If the receptacle 12 is to be removed each time the distal ends 30 and 32 of catheter 34 are to be accessed, there is no need to include outlet 16 and removable outlet 20. Thus, outlet 16 and removable outlet cover 20 are optional. Put another way, apparatus which do not include such an outlet and outlet cover are within the scope of the present invention.

In an alternate approach, after a period of time with receptacle 12 secured to patient 36 and distal ends 30 and 32 in chamber 22, it is desired to have access to the distal ends, for example, to perform a necessary medical treatment on the patient. Pull tab 50 is manually pulled to remove outlet cover 20. This exposes outlet 16 and allows access to distal ends 30 and 32 through the outlet. In this manner, the basic securement of receptacle 12 to patient 36 remains undisturbed while, at the same time, allowing access to the distal ends 30 and 32 through outlet 16. Once the medical treatment has been accomplished, the distal ends 30 and 32 of catheter 34 are passed back through outlet 16 into chamber 22. Outlet cover 20 is then replaced over outlet 16 to completely cover the outlet and provide an effective liquid tight seal.

Using this approach, the receptacle 12 can remain secured to patient 36 for relatively long periods of time, for example, on the order of about 5 days or about 10 days or more, while the patient is medically treated using catheter 34 a number of times. The use of outlet cover 20 and outlet 16, as described herein, is particularly advantageous when it is desired to protect the distal ends 30 and 32 and exit site 53 continuously on a long-term basis and/or when the patient's skin is sensitive and subject to irritation as a result of frequent applications and removals of adhesives.

FIG. 4 illustrates another embodiment of the present apparatus. Unless expressly stated otherwise, the apparatus shown in FIG. 4, shown generally at 110, is structured and functions similarly to apparatus 10. Components of apparatus 110 which correspond to components of apparatus 10 bear the same reference numerals increased by 100.

The primary difference between apparatus 110 and apparatus 10 has to do with adhesive tabs 54 and 56. Adhesive tabs 54 and 56 are secured, for example, adhesively secured, to second sidewall 126 at a position near the bottom 58 of receptacle 112. For example, adhesive tabs 54 and 56 can be individual pieces of single sided medical adhesive tape.

Each of the adhesive tabs 54 and 56 is sized to extend beyond the border (or periphery) of receptacle 112 so as to be effectively secured to the patient 36 in whose body indwelling catheter 34 is located. Each of the adhesive tabs 54 and 56 can be wrapped around the periphery of receptacle 112 and temporarily secured to the first sidewall.

When it is desired to use adhesive tabs 54 and 56, apparatus 110 is secured to patient 36 in a manner substantially as described with regard to apparatus 10. At this point, the extending ends 60 and 62 of adhesive tabs 54 and 56, respectively, are freed from the first sidewall (or otherwise made available for adhesive securement to patient 36). The adhesive sides of extending ends 60 and 62 are then adhered to patient 36. This causes the receptacle 112 to lay closer to the body of the patient 36. This "flatter profile" of receptacle 112 is more securely attached to the patient 36, reduces the apparent size of the receptacle and distal ends 30 and 32 and may give the patient an added degree of comfort and/or confidence. The extending ends 60 and 62 of adhesive tabs 54 and 56 can be temporarily removed from the patient 36, if desired, when access to the distal ends 30 and 32 is to be gained through outlet 116. After outlet 116 is closed (and distal ends 30 and 32 are again within receptacle 112), extending ends 60 and 62 can again be attached to patient 36.

FIG. 5 illustrates an alternate embodiment of the present apparatus. Unless expressly stated otherwise, the apparatus shown in FIG. 5, shown generally at 210, is structured and functions similarly to apparatus 10. Components of apparatus 210 which correspond to components of apparatus 10 bear the same reference numerals increased by 200.

The primary difference between apparatus 210 and apparatus 10 has to do with adhesive strip 66 which, when adhesively secured to second sidewall 226, covers and seals closed outlet 216. Adhesive strip 66 is constructed as an extension of receptacle 212. In other words, the adhesive strip 66 is permanently bonded to receptacle 212 along or near bottom edge 68. Adhesive strip 66 includes an adhesive surface 70 which is effective, when the adhesive strip is folded over outlet 216 to become adhesively secured to second sidewall 226.

Ordinarily in use, adhesive strip 66 is secured to second sidewall 226 and covers and seals outlet 216. When it is desired to access the distal ends 30 and 32 through outlet 216, adhesive strip 66 is removed from second sidewall 226, leaving the outlet in an open condition. When it is again desired to close outlet 216, adhesive strip 66 is simply adhered to second sidewall 226 over the outlet. An important advantage of adhesive strip 66 is that it is permanently secured to receptacle 212 so that the risk of not being able to effectively reclose outlet 216 (for example, because the outlet cover is lost or misplaced) is substantially eliminated.

FIGS. 6 and 7 illustrate a further embodiment of the present apparatus. Unless expressly stated otherwise, the apparatus shown in FIGS. 6 and 7, shown generally at 310, is structured and functions similarly to apparatus 10. Components of apparatus 310 which correspond to components of apparatus 10 bear the same reference numerals increased by 300.

The primary difference between apparatus 310 and apparatus 10 has to do with the structure by which access to the distal ends 30 and 32 is gained while the apparatus remains secured to patient 36. Bottom portion 74 extends from and below receptacle 312 and is made up of extensions of first and second sidewalls 324 and 326. The bottom border 76 of receptacle 312 is defined by a resealable closure assembly 78, such as one or more conventional tongue and groove combinations which are commonly used on resealable food storage bags. The seal is obtained by placing (or forcing) one or more elongated tongues or projections into a corresponding number of elongated grooves or recesses. The seal is broken by removing the tongue or tongues from the groove or grooves. One example of such tongue/groove sealing systems is that commonly known as a "zip lock" which is used in food storage bags.

Below closure assembly 78, the two sheets 80 and 82 making up bottom portion 74 are sealed together along a score line 84. Although score line 84 forms a positive seal, it can, if desired, be relatively easily ruptured. Below the score line 84 the two sheets 80 and 82 are heat sealed together at bottom 86.

Apparatus 310 is initially secured to patient 36, having distal ends 30 and 32 in the chamber defined by receptacle 312, with resealable closure assembly 78 sealed and score line 84 in tact. In this configuration, apparatus 310 provides a very effective water tight seal and very effectively protects distal ends 30 and 32 against environmental moisture from outside the receptacle 312.

When it is desired to access the distal ends 30 and 32 while receptacle 312 remains secured to patient 32, the lower portion 88 is severed from the remainder of bottom portion 74 along score line 84. The seal at score line 84 is thus broken. Resealable closure assembly 78 is unsealed which opens the bottom border 76 of receptacle 312. The distal ends 30 and 32 can then be accessed through the opened bottom border 76. When it is desired to close bottom border 76, resealable closure assembly 78 is simply closed or resealed. This resealed closure assembly 78 effectively seals the distal ends 30 and 32 in the chamber defined by receptacle 312.

The present apparatus are straightforward in construction and are easy and inexpensive to produce and use. Thus, the present apparatus can be used either on a continuous basis to cover and/or protect the distal ends of indwelling catheters for relatively long periods of time, or it can be used only periodically, for example, during showering or bathing, to avoid contamination of the distal ends of the catheter. The transparent receptacle allows visual monitoring of the distal end or ends of the catheter and the exit site on the patient. The closeable outlet is very effective for providing periodic access to the medical device in the chamber without destroying the securement between the receptacle and the patient. This embodiment is particularly useful when the patient is sensitive to frequent applications and removals of an adhesive material.

While this invention has been described with respect to various specific examples and embodiments, it is to be understood that the invention is not limited thereto and that it can be variously practiced within the scope of the following claims.

What is claimed is:

1. An apparatus useful for caring for the outwardly extending portion of a device partially located within the body of a human or animal which comprises:

a receptacle defining a chamber sized and adapted to receive an outwardly extending portion of a medical treatment device partially located within the body of a human or animal, at least a portion of said receptacle being transparent, said receptacle including a permanently sealed periphery or a periphery which is resealable over a minor portion thereof when said receptacle is being used;

an inlet located in said receptacle through which the outwardly extending portion is passed to be received in said chamber; and a securement member located on said receptacle, including an adhesive surface and adapted to be adhesively secured to the body of the human or animal, provided that said apparatus includes no vent which allows continuous passage of fluid out of said receptacle when said securement member is adhesively secured to the body of the human or animal.

2. The apparatus of claim 1 wherein the outwardly extending portion is the distal end portion of an indwelling medical treatment catheter and said receptacle is adapted to cover the outwardly extending portion received in said chamber when said securement member is secured to the body of the human or animal.

3. The apparatus of claim 1 wherein the outwardly extending portion is the distal end portion of an indwelling medical treatment catheter and said receptacle is adapted to protect the outwardly extending portion received in said chamber from one or more environmental factors outside said receptacle when said securement member is secured to the body of the human or animal.

4. The apparatus of claim 1 wherein said inlet is sealed when said securement member is secured to the body of the human or animal, and wherein said receptacle is made of a single ply or layer of material and is not covered when in use.

5. The apparatus of claim 1 wherein substantially all of said receptacle is transparent and said securement member substantially surrounds said inlet.

6. The apparatus of claim 1 wherein said securement member is in close proximity to said inlet.

7. The apparatus of claim 1 wherein said receptacle is made of polymeric material.

8. The apparatus of claim 1 wherein said receptacle includes two sheets of polymeric material joined together.

9. The apparatus of claim 1 which further comprises a closable outlet in said receptacle adapted, when open, to allow access to the outwardly extending portion passing through said inlet while said securement member is secured to the body of the human or animal.

10. The apparatus of claim 9 which further comprises a closure assembly sized and adapted to be positioned to maintain said closable outlet closed and to be manipulated to allow said closable outlet to be opened.

11. The apparatus of claim 1 which further comprises at least one additional securement member, located on said receptacle spaced apart from said securement member, adapted to be secured to the body of the human or animal.

12. An apparatus useful for caring for the outwardly extending portion of a device partially located within the body of a human or animal which comprises:

a receptacle sized and adapted to receive an outwardly extending portion of a medical treatment device partially located within the body of a human or animal and including a periphery having a resealable portion located between two sealed portions;

an inlet located in said receptacle through which the outwardly extending portion is passed to be received in said chamber;

a securement member located on said receptacle and adapted to be secured to the body of the human or animal; and a closable outlet in said receptacle offset relative to said inlet and adapted, when open to allow access to the outwardly extending portion passing through said inlet while said securement member is secured to the body of the human or animal.

13. The apparatus of claim 12 wherein the outwardly extending portion is the distal end portion of an indwelling medical treatment catheter and said receptacle is adapted to cover the outwardly extending portion received in said chamber when said securement member is secured to the body of the human or animal.

14. The apparatus of claim 12 wherein the outwardly extending portion is the distal end portion of an indwelling medical treatment catheter and said receptacle is adapted to protect the outwardly extending portion received in said chamber from one or more environmental factors outside said receptacle when said securement member is secured to the body of the human or animal.

15. The apparatus of claim 12 which further comprises a closure assembly sized and adapted to be positioned to maintain said closable outlet closed and to be manipulated to allow said closable outlet to be opened.

16. The apparatus of claim 12 wherein said receptacle includes a first sidewall and a substantially opposing second sidewall, said inlet being located in said first sidewall and said closable outlet being located in said second sidewall.

17. A method of caring for the outwardly extending portion of an indwelling medical treatment catheter partially located within the body of a human or animal which comprises:

provinding an apparatus comprising a receptacle defining a chamber and including a periphery adapted to be sealed when said receptacle is secured to the body of the human or animal, an inlet in said receptacle leading to said chamber and a securement member located on said receptacle;

passing said outwardly extending portion through said inlet into said chamber; and securing said securement member to the body of the human or animal, thereby covering said outwardly extending portion of said dwelling medical treatment catheter with said receptacle.

18. The method of claim 17 wherein said securing is effective to protect said outwardly extending portion of said indwelling medical treatment catheter received in said chamber from one or more environmental factors outside said receptacle.

19. The method of claim 17 wherein said apparatus includes a closable outlet in said receptacle, and said method further comprises opening said closable outlet while said securement member is secured to the body of the human or animal to access said outwardly extending portion passing through said inlet and, thereafter, closing said closable outlet.

20. The apparatus of claim 1 wherein said periphery is sealed.

21. The apparatus of claim 1 wherein a portion of said periphery is openable and resealable when said receptacle is being used.

22. The method of claim 19 wherein said closable outlet is offset relative to said inlet and which includes, after said opening, passing said outwardly extending portion through said closable outlet.

* * * * *